United States Patent [19]

Bui

[11] Patent Number: 5,406,953
[45] Date of Patent: Apr. 18, 1995

[54] APPARATUS FOR MEASUREMENT OF BLOOD PRESSURE WITH ELECTRONIC AMPLIFICATION SYSTEM FOR KAROTKOFF SOUNDS

[76] Inventor: Hoanh Bui, 12803 Linda La., Stafford, Tex. 77477

[21] Appl. No.: 719,486
[22] Filed: Jun. 24, 1991
[51] Int. Cl.⁶ ............................................. A61B 5/0225
[52] U.S. Cl. ..................................... 128/677; 128/681
[58] Field of Search ............... 128/677, 679, 680, 681, 128/686

[56] References Cited

U.S. PATENT DOCUMENTS

| | | |
|---|---|---|
| 2,405,265 | 8/1946 | Alpine . |
| 2,753,863 | 7/1956 | Bailey . |
| 3,552,383 | 1/1971 | Krueger . |
| 3,885,551 | 8/1975 | Massie . |
| 4,058,117 | 11/1977 | Kaspari et al. . |
| 4,313,445 | 2/1982 | Georgi ................................ 128/680 |
| 4,473,080 | 9/1984 | Paavola et al. ....................... 128/678 |
| 4,607,641 | 8/1986 | Fukushina ............................ 128/680 |
| 4,890,625 | 1/1990 | Sorensen ............................. 128/680 |
| 5,002,061 | 3/1991 | Close et al. .......................... 128/677 |
| 5,031,630 | 6/1991 | Hirano et al. ........................ 128/680 |

Primary Examiner—Lee S. Cohen
Assistant Examiner—Kevin Pontius

[57] ABSTRACT

An instrument for measuring the blood pressure and for checking the heart rate. It comprises of an electronic circuit for detecting, filtering, and amplifying the full steam of Korotkoff sounds which is produced as electrical signals from an acoustic pickup applied to the brachial artery. Korotkoff sounds are heard directly via the instrument's loud speaker, thus eliminating the need for the conventional stethoscope. Evaluation of blood pressure is easily and efficiently carried out by an individual with little skill or training and without the aid of a second person.

1 Claim, 5 Drawing Sheets

APPARATUS FOR MEASUREMENT OF BLOOD PRESSURE WITH ELECTRONIC AMPLIFICATION SYSTEM FOR KAROTKOFF SOUNDS

FIELD OF INVENTION

This invention relates to an improvement of the conventional technique and apparatus for measurement of blood pressure by adding an electronic amplification system which makes the Korotkoff sounds audible directly to the operator, thus eliminating the need for a stethoscope and enabling an individual to check his/her own blood pressure without the aid of a second person.

BACKGROUND - DESCRIPTION OF THE PRIOR ART

As generally accepted, the most reliable method to measure the blood pressure is by indirect auscultation. The technique consists of using an air pressure cuff as an artery occlusion device and a stethoscope for detecting the Korotkoff sounds. The inflatable cuff is applied surrounding the upper portion of the patient's arm. A hand-held air pump is used to quickly inflate the cuff to a pressure above the presumed systolic pressure by about 20–30 mmHg. Thereafter, the pressure in the cuff is gradually decreased at a rate of 2–3 mmHg/seconds by means of a bleeding valve. A point is reached at which the occluded artery begins to open briefly during each cardiac systole. At this point, the air pressure in the cuff is considered equal to the blood pressure in the brachial artery and is accepted in the medical art as systolic blood pressure.

As the pressure in the cuff continues to drop, a point is reached at which the brachial artery becomes fully open during the entire cardiac cycle. The heart is at rest at this time. This pressure is understood as diastolic blood pressure.

As mentioned above, the operator uses a stethoscope to detect the Korotkoff sounds. Korotkoff sounds are caused by the pulsating blood flow during the cardiac cycle. These sounds are generated according to a characteristic sequence well established since Korotkoff proposed his auscultation method: sound suddenly appears, changes in character, and gradually disappears. Systolic pressure is read when the first of two consecutive sounds appears during the deflation procedure. Diastolic blood pressure corresponds to the "muffling" of sound (first diastolic) and the total disappearance of sound (second diastolic).

The listening device—the cup of the stethoscope is applied over the artery, downstream to the inflated cuff to pick up the sounds generated by the pulsating blood flow in the compressed artery. However, Korotkoff sounds are low in amplitude and frequency with the band-width extending from 25 to 200 Hz. It is almost at the limits of the capability of the human ear. It is hard for the human ear to extract the true Korotkoff sounds from the background noises. Medical personnel making such measurements are required to make rather difficult determinations regarding the presence or absence of Korotkoff sounds in the context of ambiguous signals generated by artifacts. In other words, there are risks of misinterpretation and inaccuracy in the absence of experience and good training on the part of the operator.

Unfortunately, the majority of hypertensive patients have no formal training on how to use the instrument and above all, cannot afford to see the doctor on a regular basis. Therefore, they choose to check their blood pressure at home, using the conventional cuff and the very familiar stethoscope despite the lack of training in that operation.

To date, various attempts have been made to help hypertensive patients to check their own blood pressure and to eliminate the aforementioned deficiencies by mechanizing the technique and apparatus. The easiest instruments to use, though very costly, are electronic with digital displays, and LED's to provide readout of systolic and diastolic levels. Nevertheless, these electronic devices are overly sensitive to artifacts and noises and appears in many instances less accurate than the manual procedures. Consequently, automatic devices have experienced only limited acceptance by the medical profession. Doctors and nurses in the hospital and hypertensive patients at large remain fidel to the conventional method, using the blood pressure cuff and the stethoscope.

The stethoscope is primarily an instrument used for auscultation of the heart and the lung. The diaphragm housed in the cup of the stethoscope. scope is a flat surface of 3 cm. in diameter. The operator presses it very slightly to the chest wall which is another flat surface, so as to have an air seal, within the full rim, in order for the cup not to pick up noise from the environment. Now that the instrument is used to check the Korotkoff sound during the blood pressure measurement, the difficulty arises when the diaphragm is applied to the arm which is a curved surface, such air seal is obtained only when the operator presses firmly. This in turn, creates some kind of additional pressure to the brachial artery which alters the normal sequence of production of Korotkoff sounds, adding more inaccuracy in the reading.

An individual taking his own blood pressure, usually will have his arm completely in a resting position. The other hand is used to operate the air pump to inflate or deflate the cuff. He still needs an assistant to hold the cup of the stethoscope on the brachial artery. Obviously, self-taking blood pressure measurement is an impossibility with the conventional apparatus if an assistant is not available.

To overcome the above noted difficulties, the operator usually tries to insert the cup of the stethoscope between the cuff and his arm to have a free hand. By doing so, he reduces the cuff width. The length of the arterial segment which is compressed by the cuff is an important factor that influences the accuracy of blood pressure measurement. This segment is determined by the width of the occluding cuffs. A standard cuff width should be 40% of the circumference of the arm, grossly 13 cm. for the adult. As the stethoscope cup if 4 cm. (diaphragm and peripheral rim), the insertion of that cup reduces the width of the cuff that becomes $13-4=9$ cm; causing additional source of error in the measurement of blood pressure.

During the deflation of the cuff, the operator uses his thumb and index finger to loosen the valve. As air is escaping, the pressure in the cuff should drop slowly, no more than five points per second: too rapid deflation causes error in reading and too low deflation results in venous congestion and causes false readings. A non-skilled person needs a controlled valve that allows air to escape at a constant rate.

SUMMARY OF THE INVENTION

The present invention is to provide a device for indicating blood pressure which is simple in construction, economical to manufacture, effective and efficient to use, allowing an individual to measure his own pressure without the need of a stethoscope or the help of an assistant.

This invention is an improvement over the conventional method and apparatus for measuring blood pressure by adding an acoustic pickup device for detecting Korotkoff sounds which is generated by the blood flowing through the brachial artery. The acoustical pickup comprises of a sensitive diaphragm, substantially identical to a conventional stethoscope diaphragm. It is mounted overlying the brachial artery in the antecubital fossa of the arm. It is held by an adjustable elastic strap that keeps the device against the arm at a constant pressure. At the same time, it realizes a well seal within the rim of the cup, thereby preventing the intrusion of noise from the environment which further reduces misinterpretation.

Coupled to the rear of the diaphragm is a microphone that converts the acoustical signals from the diaphragm into electrical impulses. Electrical impulses, representative of Korotkoff sounds, are then amplified. A bandpass filter allows only signals with the frequency range in the vicinity of Korotkoff sounds to pass, thus enabling the operator to discriminate the true Korotkoff sounds from the associated artifact noises. An important feature here is that the diaphragm of the acoustic pickup is very similar to that of the conventional stethoscope. It provides a sound output very close to the sounds heard by a physical using the conventional stethoscope during a blood pressure measurement.

As state above, the present invention consists of an improvement over the conventional device by efficiently identifying the corresponding S1 indicative of systolic pressure and the corresponding S4 and S5 indicative of first diastolic and second diastolic. These Korotkoff sounds, free of artifacts, are amplified and are audible directly to the operator via the instrument's loud speaker, thus eliminating the need for a stethoscope.

OBJECTS AND ADVANTAGES

Accordingly, besides the objects and advantages of the BLOOD PRESSURE KIT described above, several objects and advantages of the present invention are:

(a) to provide a device for measuring blood pressure which is simple in construction, economical to manufacture, efficient to use and particularly adapted for self-examination.

(b) to provide a device for measuring blood pressure which includes a means for detection, filtering and amplification of Korotkoff sounds indicative of systolic and diastolic values so that the blood pressure can be accurately and easily determined by a person with little skill or training.

(c) to provide an electronic amplification system with a loud speaker making Korotkoff sounds audible directly to the operator, thus eliminating the need for a stethoscope and at the same time, allowing an operator who has hearing loss or is wearing a hearing aid to process the blood pressure measurement without any inconvenience.

(d) to provide the acoustic pickup with a small diameter so as to fully adapt to the antecubital fossa (anterior aspect of the arm), realizing a well seal within the rim of the cup thereby preventing the intrusion of noises from the environment and further reducing the human factor of misinterpretation.

(e) to provide the acoustic pickup retained by an adjustable elastic strap that fits snugly but not tightly as well as keeps the acoustic pickup at a constant pressure during the measurement process which further reduces the margin of errors in the measurement.

(f) to provide an acoustic pickup remaining outside of the cuff, not inserted below the cuff and not reducing the width of the cuff, thus eliminating another source of error in the reading of blood pressure so frequently observed during blood pressure measurement by a lay person.

(g) to provide a bleeder valve calibrated once at the factor; allowing air to escape at a specific rate reducing the risk of too rapid or too slow deflation of the cuff when that bleeder valve is operated by an unskilled operator.

(h) to provide an acoustic pickup with a diaphragm similar to the diaphragm of the conventional stethoscope so it can have a sound output very close to the sound heart by a physician using the conventional stethoscope.

DETAILED DESCRIPTION

Figure 1:
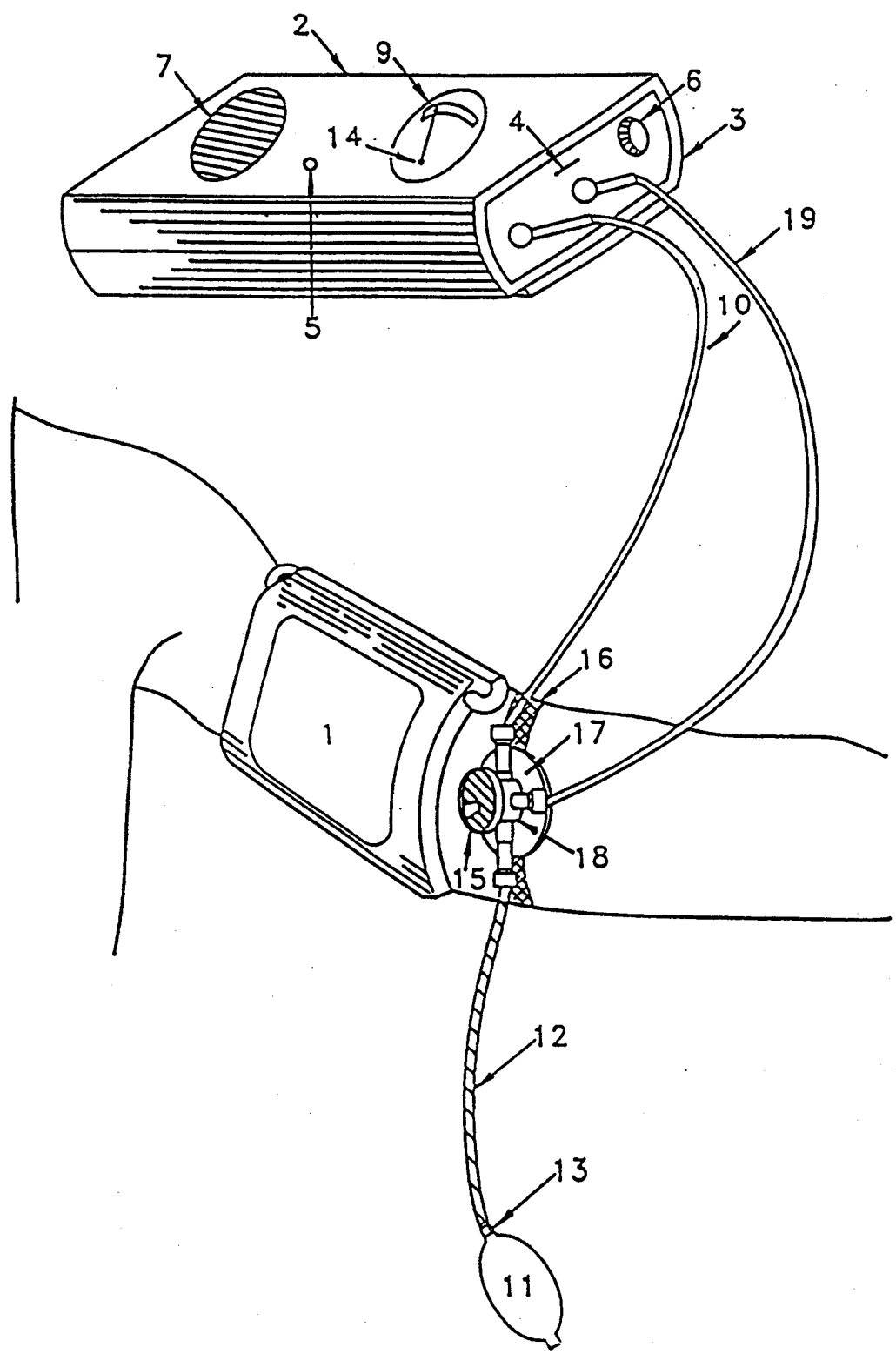
FIG. 1 is a perspective view of an apparatus for measuring blood pressure according to the present invention.

REFERRING TO FIG. 1. There is shown a blood pressure measuring apparatus comprising of an inflatable cuff assembly (1) and an electronic assembly (2) having a front panel (3).

Panel (3) provides a power on/off switch (4) volume control (6) and ready light indicator (5). The power switch (4) is operable for applying power to the apparatus and the LED light (5) is illuminated when the apparatus is ready for use.

The speaker (7) is located behind the perforation of the front panel (3), which allows the operator to hear the Korotkoff sounds as is normally done with a stethoscope by a physician when measuring blood pressure in a conventional manner.

To the left of the electronic assembly, there is shown an inflatable cuff assembly (1) of ordinary construction which is connected to an aneroid gauge (9) by a flexible tubing (10). A pneumatic pump in the form of a handheld bulb (11) is connected to the inflatable cuff by a flexible tubing (12). The bulb is provided with a quick bleeding valve (13). Attached to the aneroid gauge is a leak valve (14) which allows the air from the blood pressure cuff to gradually escape at a constant speed of 3 mmHg/second to reduce the pressure in the cuff. This leak valve is calibrated once at the factory.

Since the blood pressure cuff assembly does not form part of the present invention, any conventional standardized blood pressure cuff may be used. No details of the components of the blood pressure cuff have been illustrated.

Figure 2:
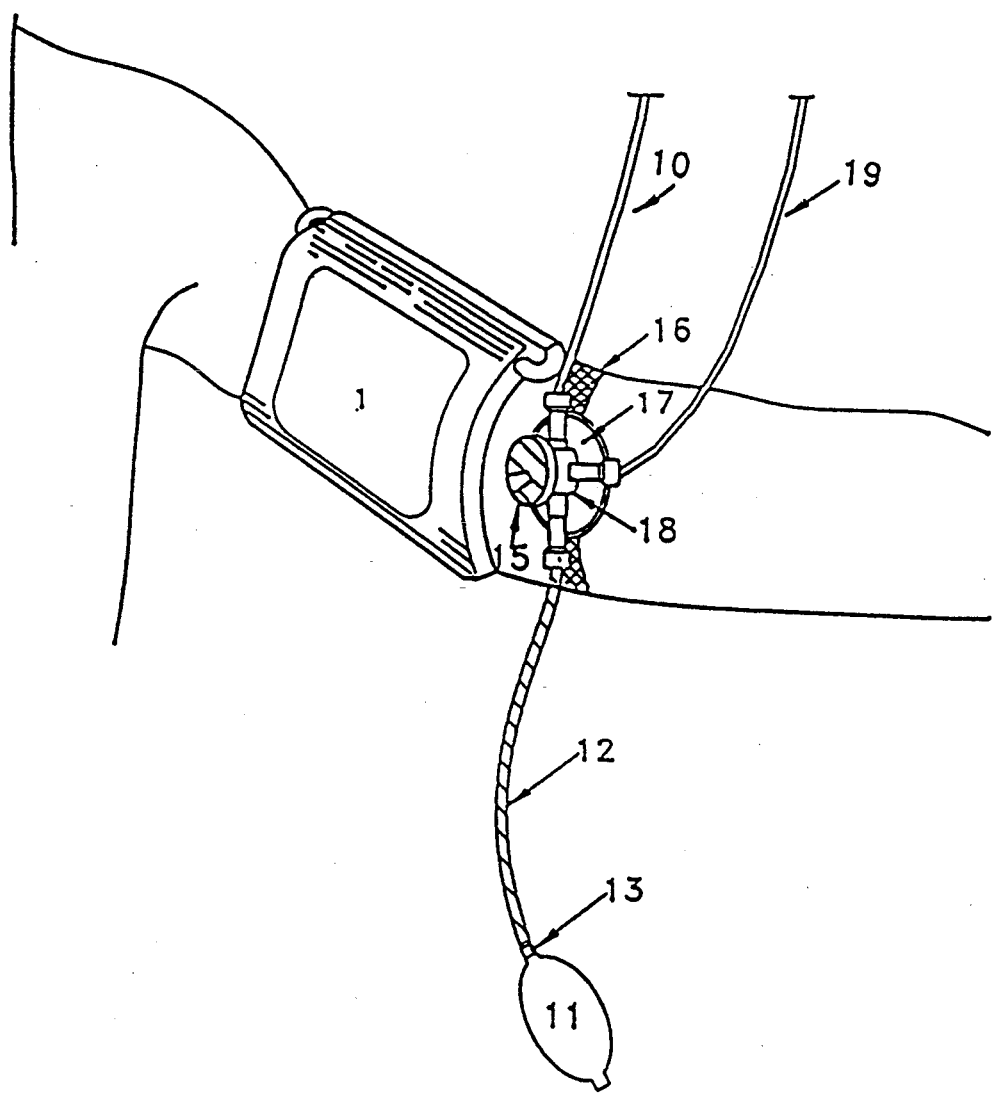
FIG. 2 is a perspective view of the acoustic pickup in place in the antecubital fossa, overlaying the brachial artery and retained by adjustable strap.

REFERRING TO FIG. 2: An acoustic pickup (15) adjacent to the blood pressure cuff (8) and at 1½" below its distal margin. The acoustic pickup is retained at the antecubital fossa over the brachial artery by an adjustable elastic strap (16) that keeps the acoustic pickup tight enough to realize a complete seal within the rim of the acoustic pickup. Housed inside the acoustic pickup is an acoustically responsive diaphragm (17) identical to that of a conventional stethoscope, which is capable to vibrate in response to the acoustic input for generating an acoustic signal.

Adjacent to the diaphragm (17) is a microphone (18) that converts the acoustic signal into electrical impulses. The output of the microphone (18) is connected to the amplification circuit via a wire, (19) plug and jack. The microphone (18) is of the type used for general amplification.

Proper placement of the cuff assembly (1) and particularly the acoustic pickup (15) on the subject's arm is important for obtaining correct blood pressure measurement. It is well established that the acoustic pickup must be placed over the brachial artery: the closer the sensor is to artery, the better will be the signal to noise ratio.

Figure 3:
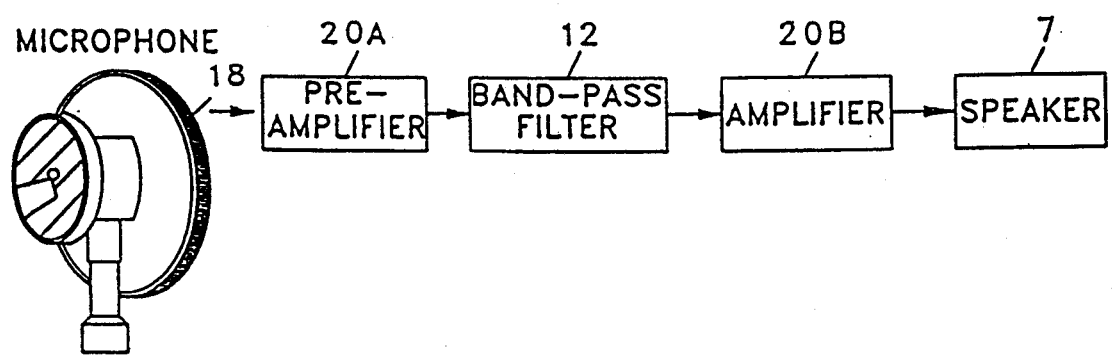
FIG. 3 is a block diaphragm of a generalized sphymomanometer system incorporating features of the present invention.

REFERRING TO FIG. 3: Coupled to the output of the microphone (18) is an audio frequency amplifier circuit means (20A–20B). The circuit is provided for amplifying the output of the microphone signals. Included in the amplifier circuit is a band-pass filter (21) to eliminate the vibration related to ambient noise and to allow only signals within the frequency range of Korotkoff sounds to pass. Coupled to the amplification circuit is the speaker (7) making Korotkoff sounds audible directly to the operator.

Figure 4:
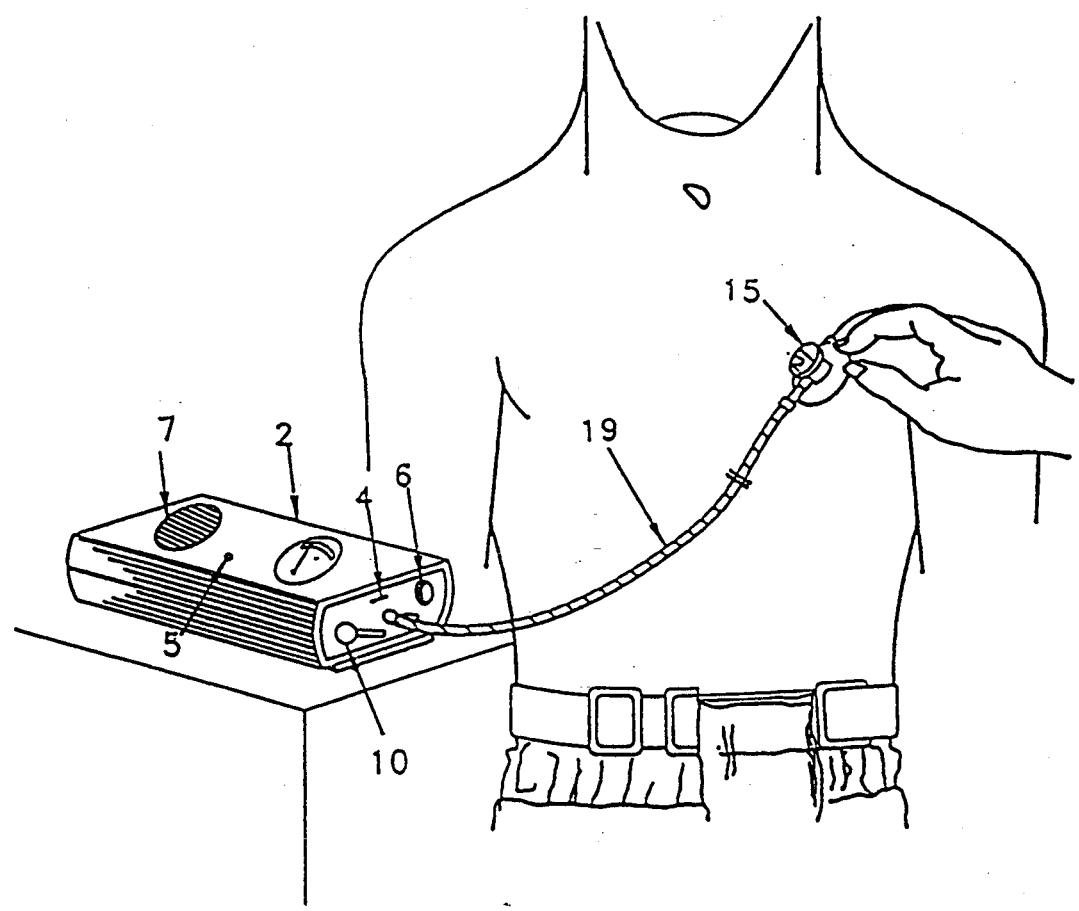
FIG. 4(a) is a perspective view of another embodiment of the present invention having no aneroid gauge, but does have an auxiliary acoustic pickup used to hear the heart beat.
Figure 5A:
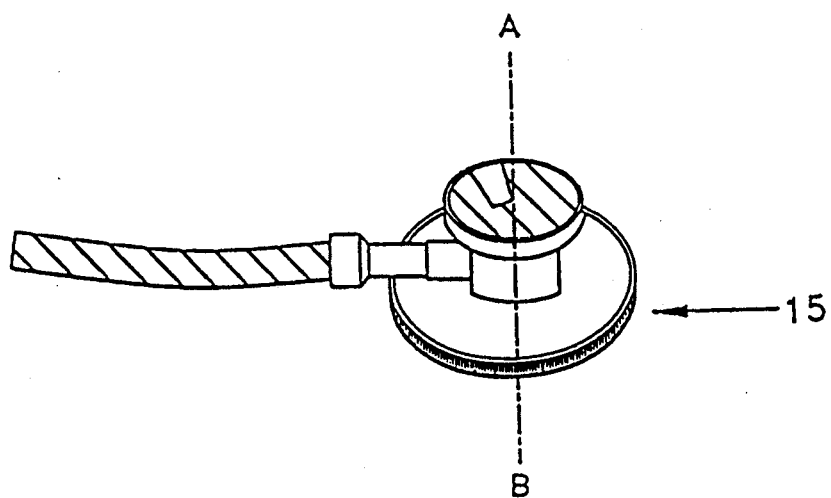
FIG. 5(a) is a perspective view of the acoustic pickup.
Figure 5B:
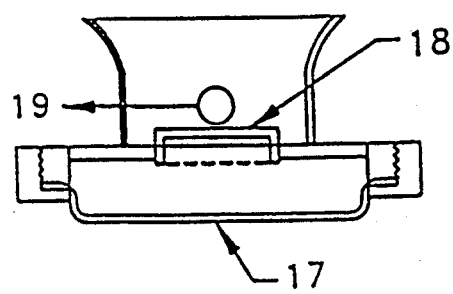
FIG. 5(b) is a perspective view of the acoustic pickup and a cross-sectional view along line A-B.

REFERRING TO FIG. 4(a) and (b): There is shown an additional acoustic pickup used for checking the heart beats.

REFERENCE NUMERALS IN DRAWINGS:

1. Inflatable cuff assembly
2. Electronic assembly
3. Front panel
4. On - off switch
5. LED
6. Volume control
7. Speaker
8. Bladder
9. Aneroid gauge
10. Flexible tubing from bladder to aneroid gauge
11. Hand-held bulb
12. Flexible tubing from bulb to bladder
13. Dump valve
14. Bleed valve (leak valve)
15. Acoustic pickup
16. Strap
17. Acoustic diaphragm
18. Microphone
19. Wire from microphone to amplification circuit
20. Amplifier
21. Band-pass filter A preferred embodiment of the invention has been described herein. It is understood, however, that a variety of changes made in the details of the apparatus and their arrangement may also be made within the spirit and scope of the present invention. It is intended that the scope and the spirit of the invention should not be restricted to the embodiment described, rather be determined by reference to the claims hereinafter provided.

I claim:

1. An apparatus for measuring the blood pressure of an adult subject having an arm with a brachial artery, an elbow, and a cubital fossa, said apparatus comprising:

a cuff means for occluding the brachial artery of the subject by inflation;

an inflation means, coupled to said cuff means, for inflating said cuff means;

a pressure changing means, coupled to said cuff means, for gradually changing the pressure in said cuff means;

a meter means, coupled to said cuff means, for measuring the instantaneous pressure in said cuff means and for displaying said instantaneous pressure to the subject;

a means for detecting Korotkoff sounds and for converting these Korotkoff sounds into electric signals, wherein said means for detecting and converting comprises:

a cup-shaped member having a rim and a base, an acoustically responsive diaphragm mounted over the rim of the cup-shaped member, a miniature microphone, mounted at the center of the base of the cup-shaped member, which produces electric signals, and a means for retaining the cup-shaped member over the cubital fossa of the arm of the subject;

an amplifier means, coupled to said means for detecting and converting, for amplifying said electric signals and thereby producing amplified electric signals;

an output means, coupled to said amplifier means, for converting said amplified electric signals into audio acoustic pressure waves which are perceivable by the subject.

* * * * *